(12) United States Patent
Bornvall

(10) Patent No.: US 10,973,474 B2
(45) Date of Patent: Apr. 13, 2021

(54) LOWER-BODY RADIATION PROTECTION SYSTEM

(71) Applicant: Borntech, Färjestaden (SE)

(72) Inventor: Ove Bornvall, Färjestaden (SE)

(73) Assignee: BORNTECH, Farjestaden (SE)

( * ) Notice: Subject to any disclaimer, the term of this patent is extended or adjusted under 35 U.S.C. 154(b) by 227 days.

(21) Appl. No.: 16/300,682

(22) PCT Filed: May 10, 2017

(86) PCT No.: PCT/EP2017/061142
§ 371 (c)(1),
(2) Date: Nov. 12, 2018

(87) PCT Pub. No.: WO2017/194583
PCT Pub. Date: Nov. 16, 2017

(65) Prior Publication Data
US 2019/0209105 A1    Jul. 11, 2019

(30) Foreign Application Priority Data
May 12, 2016 (SE) .................................... 1650639-6

(51) Int. Cl.
*A61B 6/10* (2006.01)
*G21F 3/00* (2006.01)
*A61B 6/04* (2006.01)

(52) U.S. Cl.
CPC ................ *A61B 6/107* (2013.01); *G21F 3/00* (2013.01); *A61B 6/0407* (2013.01)

(58) Field of Classification Search
CPC .... A61B 6/00; A61B 6/10; A61B 6/44; A61B 6/107; A61B 6/462; A61B 6/467;
(Continued)

(56) References Cited

U.S. PATENT DOCUMENTS

| 5,006,718 A | 4/1991 | Lenhart |
| 6,023,800 A | 2/2000 | Stickley |

(Continued)

FOREIGN PATENT DOCUMENTS

| DE | 297 06 322 U1 | 6/1997 |
| DE | 201 12 678 U1 | 10/2001 |

(Continued)

OTHER PUBLICATIONS

International Search Report and Written Opinion for International Application No. PCT/EP2017/061142, dated Jul. 26, 2017.

*Primary Examiner* — David E Smith
*Assistant Examiner* — Hsien C Tsai
(74) *Attorney, Agent, or Firm* — Xsensus LLP

(57) ABSTRACT

The invention refers to an elongated base profile (7) for use in a lower-body radiation protection system. The elongated base profile (7), comprises as seen in a transverse cross section, a first connecting portion (8) adapted to engage a connection rail (4) of an examination table (1), a second connecting portion (14) forming a protrusion (15) or a groove extending along the longitudinal extension of the elongated base profile (7), wherein the protrusion (15) is adapted to form a connection rail (4), and wherein the groove is adapted to support a separate connection rail or a separate connector; and a third connecting portion (18) adapted to engage a first connector (11) of a first shielding panel (10).

11 Claims, 6 Drawing Sheets

(58) Field of Classification Search
CPC ... A61B 6/0407; A61B 6/0457; A61B 6/4405; A61B 6/4441
See application file for complete search history.

(56) References Cited

U.S. PATENT DOCUMENTS 6,499,158 B1 12/2002 Easterling
2005/0081295 A1 4/2005 Malcolm

FOREIGN PATENT DOCUMENTS

| DE | 203 09 157 U1 | 8/2003 | |
|----|----|----|----|
| DE | 20309157 U1 * | 8/2003 | ............... E04D 3/06 |
| WO | 2010/146109 A1 | 12/2010 | |

* cited by examiner

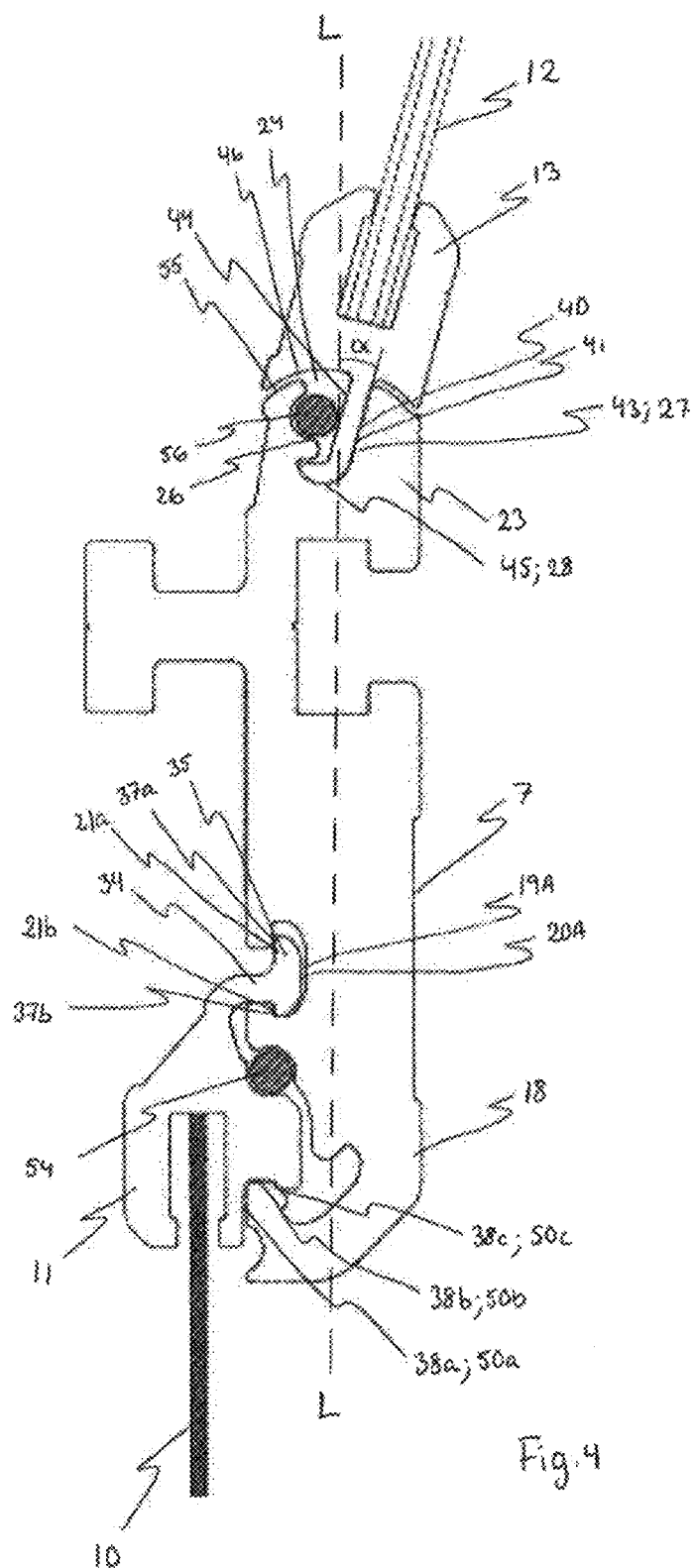

LOWER-BODY RADIATION PROTECTION SYSTEM

CROSS-REFERENCE TO RELATED APPLICATIONS

This application is a National Stage Application based on PCT/EP2017/061142, filed 10 May 2017, and claims priority to Swedish Patent Application No. 1650639-6, filed 12 May 2016, the entire contents of which being incorporated herein by reference.

FIELD OF THE INVENTION

The present invention relates to an elongated base profile for use in a lower-body radiation protection and a lower-body radiation protection system.

BACKGROUND OF THE INVENTION

In order to keep the radiation exposure caused by radioscopy as low as possible for the people involved in treatment it is well known to use radiation protective clothing. However, such clothing is not sufficient due to the multidirectional nature of the radiation and also secondary radiation. To reduce such radiation it is well known to additionally use a lower-body protective arrangement. A lower-body protective arrangement is infact an integral part of every radiation protection concept for interventional radiology. The lower-body protector shields the examiner against secondary radiation emanating from the body of the patient. The protection absorbs radiation from underneath the table and shields the lower extremities and genital area of the examiner.

In principle, a lower-body arrangement according to prior art comprises an upper shielding panel and a lower shielding panel, which both are made of an X-ray shielding material. The lower shielding panel extends all the way down to the floor, whereas the upper shielding panel has a limited vertical extension to allow access to the patient.

As a common feature to the known lower-body protective arrangements, they are generally mounted to a support rail that is arranged to the examination table.

A first general principle, is known from e.g. WO10146109, in which the shielding panels are mounted to a connector that is hung and screwed to the supporting rail.

Yet another typical example is disclosed in U.S. Pat. No. 5,006,718, in which a pivotable arm supporting an upper and a lower shielding panel is connected to the support rail of the examination table. The arm is pivotable in the horizontal plane to and from the examination table.

These prior art arrangements are however not optimal. The support rail on the examination table is not used exclusively for the lower-body protective arrangement but also for other equipment relating to the overall examination process. One such example is the control panel for the operation of the examination table which is also mounted to the support rail. For the lower-body protective arrangement not to interfere with such equipment, the equipment is typically arranged along the support rail and adjacent the lower-body protective arrangement. This does however not provide the optimal ergonomy to the examiner who have to stretch or turn to reach the equipment. Hence, there is a risk that the examiner refrains from using the lower-body protective arrangement properly, thereby risking his/her own health and safety.

It is further a well known fact that a radiation shielding should be arranged as close to the radiation source as possible to have the best effect.

Hence, the object of the present invention is to provide a lower-body protection system that promotes an ergonomic working environment.

Another object is that the shielding panel should be easy to install but also to remove to allow uncomplicated patient transfers and also in case of emergency.

Yet another aspect is that all parts should be easy to clean in order of maintaining a high level of hygiene.

SUMMARY OF THE INVENTION

It is noted that the invention relates to all possible combinations of features recited in the claims.

According to a first aspect, the invention relates to an elongated base profile for use in a lower-body radiation protection system, wherein the elongated base profile, as seen in a transverse cross section, comprises: a first connecting portion adapted to engage a connection rail of an examination table, and a second connecting portion forming a protrusion or a groove extending along the longitudinal extension of the elongated base profile, wherein the protrusion is adapted to form a connection rail, and wherein the groove is adapted to support a separate connection rail or a separate connector; and a third connecting portion adapted to engage a first connector of a first shielding panel.

In the context of the invention the term panel is to be interpreted, unless nothing else is explicitly given, as a rigid panel or a flexible drape or curtain.

The elongated base profile constitutes a support structure which when permanently mounted to the connection rail of the examination table serves mainly two functions. First of all, it is arranged to support a first shielding panel which is adapted to be mounted thereto via a first connector. The first shielding panel may be an essentially vertically hanging panel which extends from the examination table towards the floor. Secondly, the protrusion or groove of the second connecting portion allows supporting and mounting of equipment such as control panels etc. which in prior art solutions are supported and mounted directly to the connection rail of the examination table. Thereby, the ergonomic conditions for the operator will be greatly improved since he/she will get a closer access to the examination table and hence to the patient. Also, he/she will always have direct access to equipment such as control panels etc. since they may be mounted to or supported by the protrusion or groove of the elongated base profile and thereby be arranged on the same side of the shielding panel as the operator. Also, the position of such devices along the protrusion or groove of the base profile may be freely determined without having to consider or be restricted to where and how the lower-body radiation system is mounted to the examination table.

The base profile is very easy to clean although the relatively complex cross sectional geometry. The elongated profile has a uniform cross section whereby all surfaces may be easily cleaned by wiping off with a cloth or a brush. The cloth or brush may be slid along the rail with its grooves and protrusions and may even be tailor made with a complementary profile. The same applies to the first and second connectors which are arranged to engage the base profile.

The first connecting portion and the second connecting portion may be arranged on opposite sides of the elongated base profile.

The first connecting portion may be formed by a recess having a cross sectional shape complementary to the cross sectional shape of the connection rail of the examination table, and wherein the recess may be adapted to engage the connection rail of the examination table. Hence, the elongated base profile may be said to constitute a distance member that uses an existing connecting rail as mounting and support while forming a new displaced connecting portion, i.e. the second connecting portion which as such may serve the same function as the connection rail of the examination table.

The protrusion formed by the second connecting portion may have a cross sectional shape corresponding to the cross sectional profile of the connection rail of the examination table. Accordingly, the elongated base profile uses an existing connection rail as its support, while at the same time forming a new similar connection rail.

The third connecting portion may comprise a recess, and the first connector of the first shielding panel may comprise a protrusion, whereby the first connector of the first shielding panel may be arranged to engage the third connecting portion by the protrusion being inserted into the recess by a linear movement and then pivoted inside the recess into a locking position.

The linear movement may be made in a direction substantially perpendicular to the extension of the bottom wall of the recess. Once the protrusion of the first connector linearly engages the recess of the third connecting portion, the operator may pivot the first shielding panel into a locking position. Hence, the mounting of the first shielding panel may be made by an operational movement that extends mainly perpendicular to the longitudinal side of the examination table without the operator having to make any undue twisting of his torso. Thereby, the ergonomic is very beneficial.

The third connecting portion may comprise at least two recesses, each recess allowing a major surface of the first shielding panel to extend in a preset angle in view of a horizontal direction in a state when the first connector of the first shielding panel is set to a locking position. The first recess may by way of example be arranged to allow the first shielding panel to extend essentially in the vertical direction, while the second recess may be arranged to allow the panel to form an angle of 45° to the vertical direction.

The elongated base profile may further comprise a fourth connecting portion adapted to engage a second connector of a second shielding panel. The fourth connecting portion may comprise a recess, and the second connector of the second shielding panel may comprise a protrusion, whereby the second connector of the second shielding panel may be arranged to engage the fourth connecting portion by the protrusion being inserted into the recess by a linear movement and then pivoted inside the recess into a locking position. It is preferred that the main plane of the second shielding panel, when the second connector lockingly engages the recess of the fourth connecting portion forms an angel in a direction towards the examination table. Thereby it will not unduly interfere the work of the operator and also not cause any inconvenience to the patient's comfort. The angle may e.g. be in the range of 10-20° in view of the vertical direction.

According to a second aspect, the invention relates to a lower-body radiation protection system, comprising: an elongated base profile which, as seen in a transverse cross section, comprises: a first connecting portion adapted to engage a connection rail of an examination table, and a second connecting portion forming a protrusion or a groove extending along the longitudinal extension of the elongated base profile, wherein the protrusion is adapted to form a connection rail, and wherein the groove is adapted to support a separate connection rail or a separate connector; and a first connector of a first shielding panel, the first connector being adapted to be connected to a third connecting portion of the elongated base profile.

The lower-body radiation system is based on the same components as have been discussed above, and to avoid undue repetition, reference is made to the arguments given above.

The lower-body radiation protection system may further comprise a second connector of a second shielding panel, the second connector being adapted to be connected to a fourth connecting portion of the elongated base profile.

The elongated base profile, the first connector and the second connector may be provided by extrusion. It goes without saying that all extruded parts may be made of a metallic material or a plastic material. Extrusion allows complex cross sectional geometries and also keeping of tolerances. The extruded profiles may easily be cut into customized lengths.

The first connector may be adapted to be connected to the third connecting portion of the elongated base profile via an adaptor profile.

According to yet another aspect, the invention refers to the use of an elongated base profile with the features given above on an examination table as a part of a lower-body radiation protection system.

BRIEF DESCRIPTION OF THE DRAWINGS

The above as well as additional objects, features and advantages of the present invention, will be better understood through the following illustrative and non-limiting description of preferred embodiments of the present invention, with reference to the appended drawings where the same reference numbers will be used for similar elements.

FIG. 4 discloses the elongated base profile together with a first and a second shielding panel in a position where the first and second shielding panels have been mounted thereto and set to a locking position.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
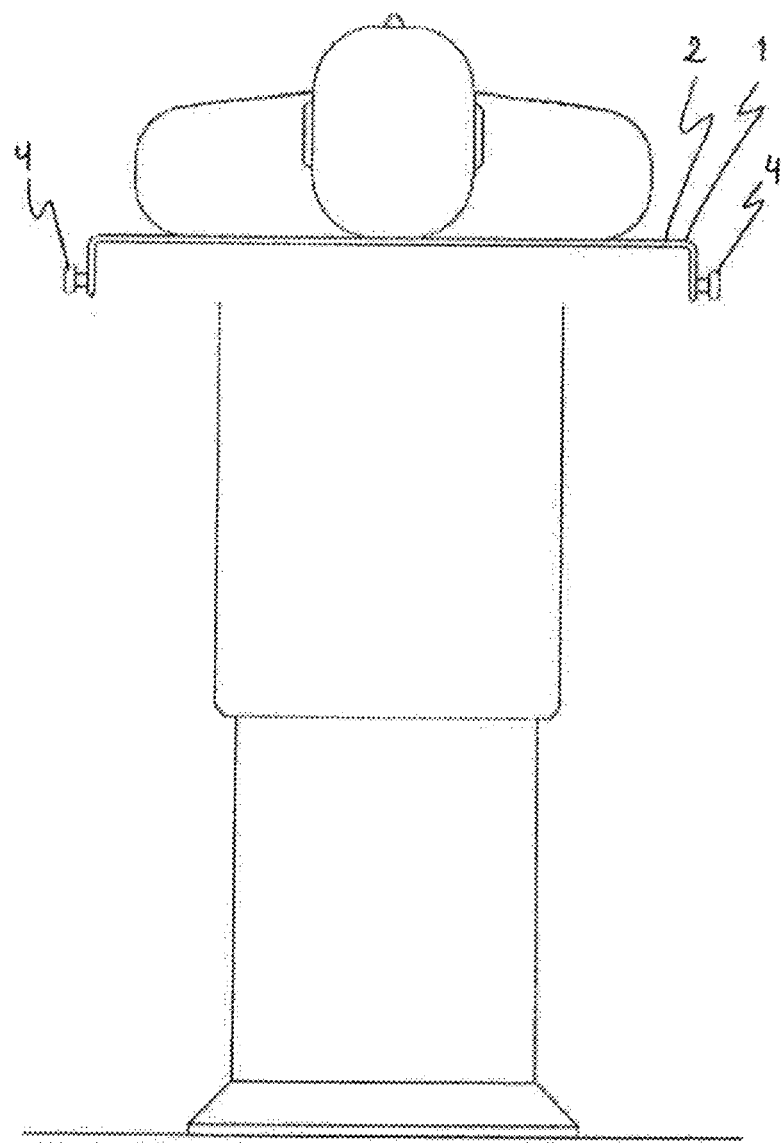
FIG. 1 schematically discloses one example of an examination table with a connecting rail mounted thereto.

Referring to FIG. 1 the overall design of an examination table 1 is disclosed. The examination table 1 comprises a bed face 2 on which the patient to be examined is positioned. The bed face 2 is supported by a support structure 3.

Each of the opposing long sides of the examination table 1 comprises a connection rail 4 which is fixedly arranged to the examination table 1. The connection rail 4 as such is well known in the art and is typically used to support equipment such as control panels etc. used to operate e.g. the examination table 1. The cross sectional shape of the connection rail 4 is typically provided as a T-shaped profile.

Figure 2:
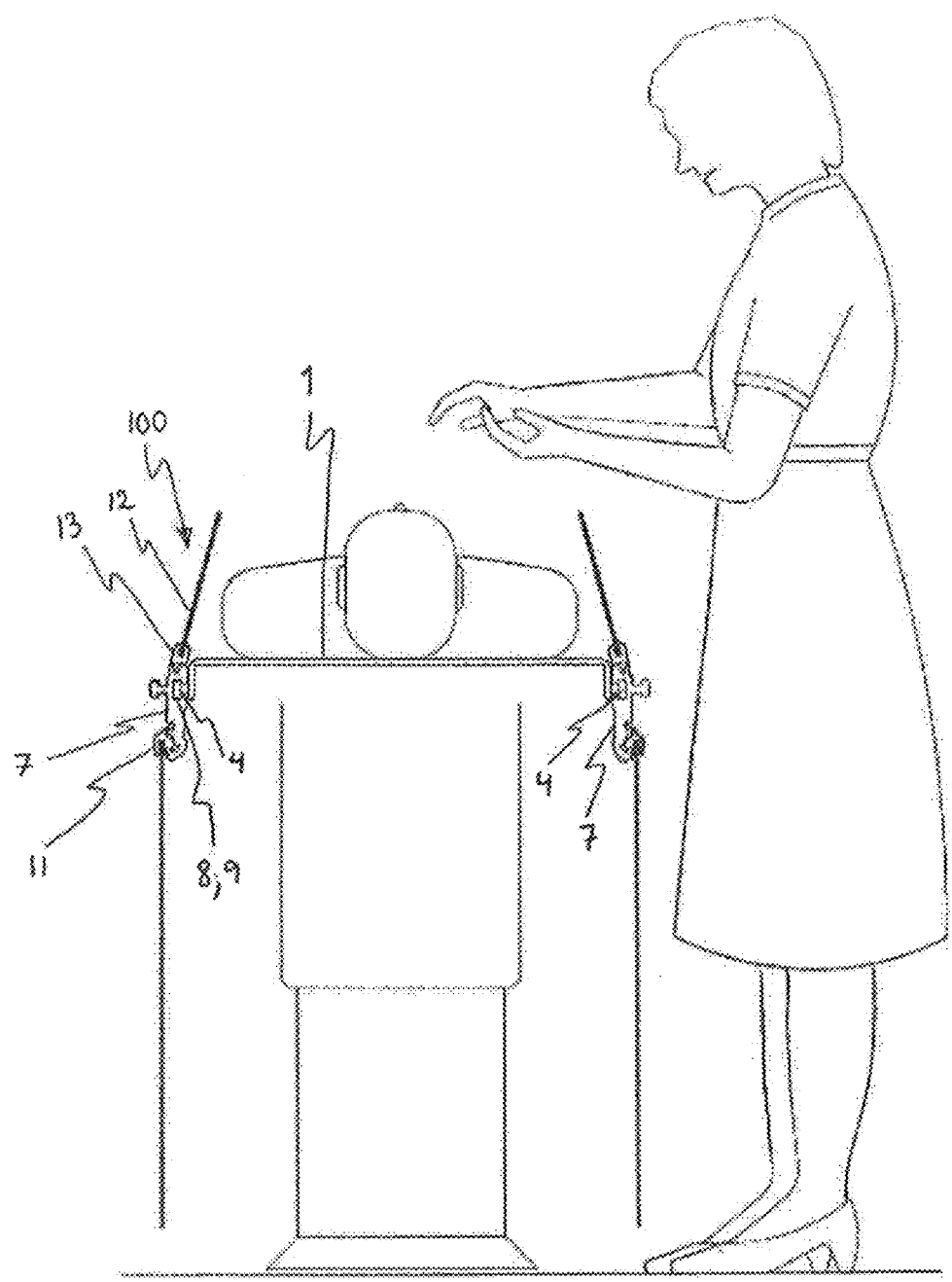
FIG. 2 discloses one embodiment of the inventive lower-body radiation protection system mounted to the connecting rail of an examination table.

Now turning to FIG. 2, the examination table 1 with its two connection rails 4 is disclosed supporting a lower-body radiation protection system 100 according to the invention.

Each connection rail 4 supports an elongated base profile 7. The elongated base profile 7 comprises a first connecting portion 8 in the form of a recess 9 adapted to engage the connection rail 4.

The base profile 7 is preferably permanently mounted to the connection rail 4 by sliding the base profile 7 along and onto the connection rail 4.

The base profile 7 supports a first shielding panel 10 which is connected thereto by a first connector 11. The first shielding panel 10 extends from the examination table 1 to the floor.

The base profile 7 further supports a second shielding panel 12 which is connected thereto by a second connector 13. The second shielding panel 12 extends from the examination table 1 in an upward direction and forms in the disclosed embodiment an angle towards the examination table 1.

Figure 3:
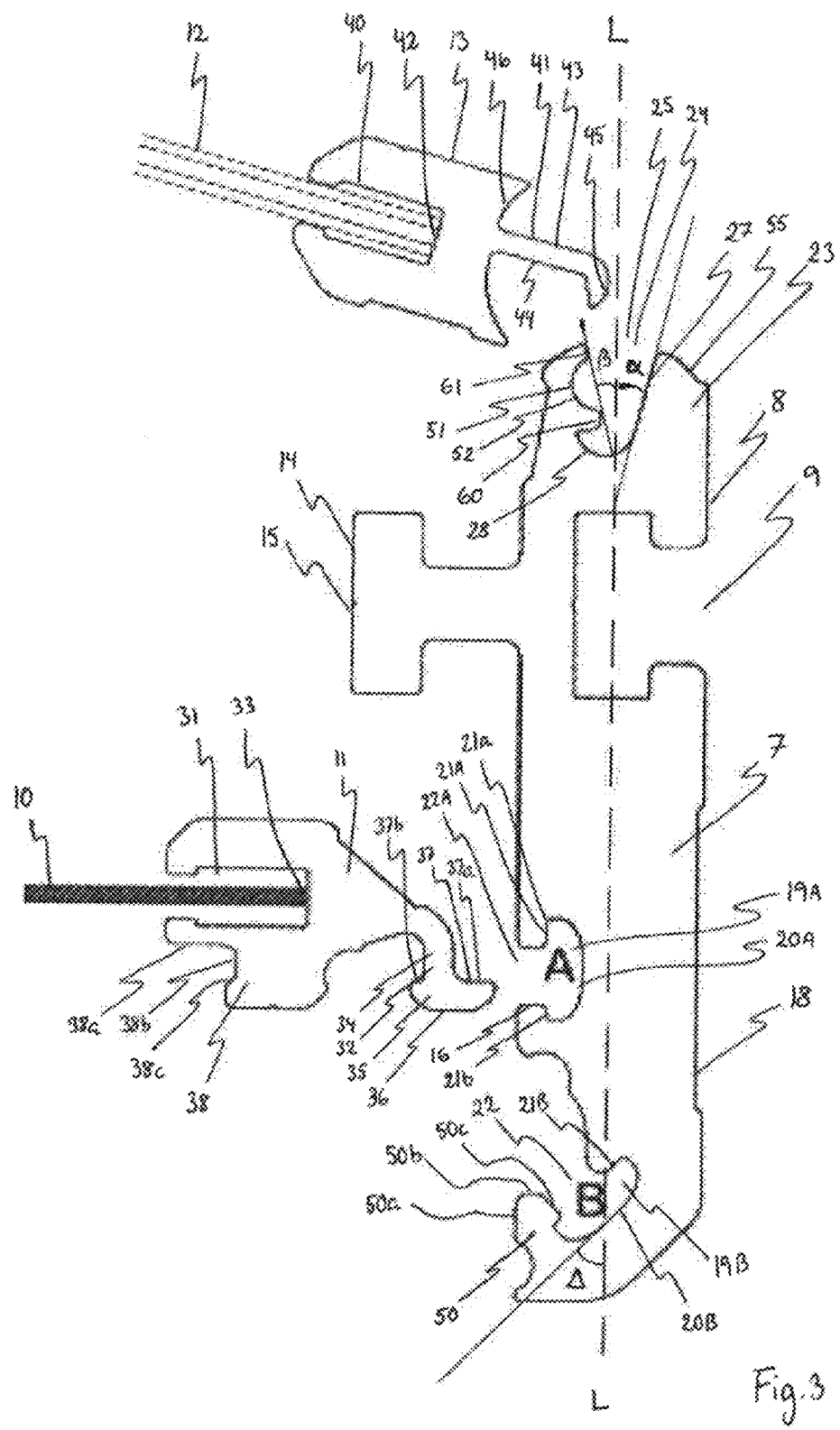
FIG. 3 discloses a cross section of the elongated base profile together with a first and a second shielding panel to be mounted thereto.

Now turning to FIG. 3, a cross section of the base profile 7 is disclosed. The elongated base profile 7 will be described as oriented to extend in a horizontal plane. Further the cross section has a center axis L which during normal use is adapted to extend in the vertical direction.

The base profile 7 comprises a first connecting portion 8 in the form of a recess 9 adapted to engage the connection rail 4 of the examination table 1. The recess 9 has a cross sectional profile corresponding to the cross sectional profile of the connection rail 4. In the disclosed embodiment, the recess 9 has a T-shaped profile. It is obvious to the skilled person that other cross sections may be used depending on the design of the connection rail 4.

The base profile 7 comprises a second connecting portion 14 in the form of a protrusion 15. In the disclosed embodiment the cross sectional profile is T-shaped. The protrusion 15 has a cross sectional profile corresponding to the connection rail 4 both in terms of geometry and dimensions. Thereby, any equipment such as control panels or the like (not disclosed) that is normally arranged to the connection rail 4 of the examination table 1 may be arranged in the very same manner to the protrusion 15.

The base profile 7 comprises in its lower end a third connecting portion 18. In the disclosed embodiment the third connecting portion 18 comprises two recess 19A and 19B, each allowing a specific locking position of the first shielding panel 10. When the first panel 10 is mounted to the recess 19A, the panel will be oriented in an essentially vertical position, whereas when the panel 10 is mounted to the recess 19B, the panel 10 will be oriented with an angle Δ to a vertical plane extending along the longitudinal center axis L of the elongated base profile 7. One of the two recesses 19A, 19B may be omitted. Also, additional recesses may be provided.

The recess 19A is defined by a bottom wall 20A and an opposite top wall 21A. The bottom wall 20A is adapted to interact with the first connector 11 of the first shielding panel 10 in a manner to be described below. The bottom wall 20A is disclosed as being slightly rounded. Both walls 20A, 21A have an essentially vertical extension when the base profile 7 is mounted to a connection rail 4.

The top wall 21A is divided by an opening 22A into a first wall portion 21a and a second wall portion 21b, both being provided as flat surfaces.

A lower wall of opening 22A presents an abutment surface 16 which is adapted to interact with the first connector 11 when the first shielding panel 10 is mounted thereto.

The recess 19B has a cross section corresponding to that of the recess 19A with the difference that the bottom wall 20B and the opposite top wall 21B are arranged with an angle Δ in view of a vertical plane extending along the longitudinal extension of the base profile 7. In the disclosed embodiment the angle Δ is about 45° and it goes without saying that other angles may be used.

The lower wall of the opening 22B forms part of a shoulder 50 which provides a first, a second and a third abutment surface 50a-50c adapted to interact with and support the first connector 11 of the first shielding panel 10 when mounted to the first recess 19A. This interaction will be discussed below.

The base profile 7 comprises in its upper end a fourth connecting portion 23. The fourth connecting portion 23 is provided as a recess 24 having a hook-like cross sectional profile with an opening 25. The fourth connecting portion 23 is adapted to engage and support the second connector 13 of the second shielding panel 12.

The opening 25 is formed between a front wall 51 and a rear wall 27. The rear wall 27 is essentially flat. The rear wall 27 forms an angle α corresponding to 10-30° in view of the longitudinal center axis L. The front wall 51 forms an angle β corresponding to 5-20° in view of said vertical plane.

The rear wall 27 merges into a single curved bottom wall 28. The bottom wall 28 merges into the front wall 51. The front wall 51 is provided with an arc-shaped recess 52 which divides the front wall into a lower shoulder 60 and an upper shoulder 61, both facing the rear wall 27.

As given above the first connector 11 of the first shielding panel 10 is adapted to engage either the first recess 19A or the second recess 19B of the third connecting portion 18.

The first connector 11 is provided as an elongated profile which as seen in cross section comprises a recess 31. The recess 31 has an essentially rectangular cross section adapted to receive an edge 33 of the first shielding panel 10.

The first connector 11 further comprises a protrusion 32. The protrusion 32 is T-shaped comprising a web 34 and a flange 35 extending on opposite sides of the web 34. The web 34 has an extension essentially perpendicular to the main plane of the shielding panel 10 whereas the flange 35 extends essentially in parallel with the main plane of the shielding panel 10. The flange 35 has a front wall 36 having a profile corresponding to the bottom wall 20A, 20B of the recess 19A and 19B. Thus, the edges of the flange 35 are slightly rounded.

The flange 35 further has a rear wall 37 which is divided by the web 34 into a first portion 37a and a second portion 37b.

The first connector 11 further comprises a locking shoulder 38 with a first, a second and a third abutment surface 38a-38c. The locking shoulder 38 with its abutment surfaces 38a-38c is adapted to interact with the first, second and third abutment surfaces 50a-50c of the shoulder 50 of the third connecting portion 18 of the base profile 7.

In the following the mounting of the first shielding panel 10 to the base profile 7 will be described based on the disclosure of FIGS. 3 and 4. The panel 10 will be described as mounted in its vertical position provided by the recess 19A.

The operator moves the first shielding panel 10 with the first connector 11 mounted thereto and with the main plane of the panel extending in a direction essentially perpendicular to the bottom wall 20A of the recess 19A. As the front wall 36 of the protrusion 32 meets the bottom wall 20A of the recess 19A, the operator moves the first shielding panel 10 in an upward direction while also pivoting the panel 10 counterclockwise. During this pivoting, the flange 35 of the first connector 11 will move inside the recess 19A. The pivoting movement will be facilitated by the front wall 36 of the flange 35 being guided by the curved bottom wall 20A of the recess 19A. As the rear wall 37a of the flange 35 abuts the top wall 21a of the recess 19A, the operator may release the grip whereby the flange 35 will slide by gravity to a resting position inside the recess 19A. In this position the panel 10 with its connector 11 will be prevented from falling out of the recess 19A by the front walls 37a, 37b of the flange 35 abutting the top walls 21a, 21b of the recess 19A.

Further, in this position the panel 10 will be prevented from being pivoted by the abutment surfaces 38a-38c abutting the corresponding abutment surfaces 50a-50c of the third connecting portion 18 of the base profile 7.

In the embodiment of FIG. 4, a voluntary locking pin 54 has been inserted in a through channel that is formed between opposing surfaces of the first connector 11 and the elongated base profile 7.

As will be understood by the skilled person, if the first shielding panel 10 with its first connector 11 instead is mounted to the lower recess 19B, the panel will be mounted with its main plane extending in an angle Δ in view of the longitudinal extension of the elongated base profile 7. However, in that position the panel will mainly be supported by the web 34 of the protrusion 32 engaging the abutment surfaces 50a-50c of the third connecting portion 18 of the base profile 7.

In the following the mounting of the second shielding panel 12 will be discussed.

The second connector 13 is provided as an elongated profile which as seen in cross section comprises a recess 40 and a protrusion 41. The protrusion 41 extends from a single-curved, concave end surface 46 of the second connector 13.

The recess 40 has an essentially rectangular cross section adapted to receive an edge 42 of the second shielding panel 12.

The protrusion 41 is formed by a first and a second opposing wall 43, 44 merging with a hook-like end portion 45. The end portion 45 has a slightly rounded wall portion.

When mounting the second shielding panel 12 with its connector 13 to the fourth connecting portion 23 of the base profile 7, the operator lifts the panel 12 and inserts the protrusion 41 into the recess 24 by letting the first wall 43 of the protrusion 41 slide against the rear wall 27 of the recess until the hook-like end portion 45 engages the bottom wall 28. In this position, the panel 13 is pivoted so that the first wall 43 of the protrusion 41 rests against the rear wall 27 of the recess 40. The main plane of the panel 12 will in this position form an angle corresponding to the angle α. By the angle, the available working space of the operator will be increased while still not negatively interfering with the comfort of the patient lying on the examination table.

The pivoting will be guided by the single-curved, concave end surface 46 of the second connector 13 sliding against a complementary single-curved end surface 55 on the fourth connecting portion 23 of the base profile 7.

To maintain the angled position of the panel 12, an optional locking pin 56 may be inserted in the interspace formed between the front wall 51 of the recess 24 and the second wall 44 of the protrusion 41.

The skilled person will understand that other angles are applicable and that the second shielding panel 12 also may be arranged to extend essentially vertically.

During normal use it is typically only the second shielding panel that must be removed when positioning a patient on the examination table. The weight of a second shielding panel including the second connector may be lower than 2 kg, whereby the mounting and removal thereof is made very convenient to the operator.

The base profile 7 with its first and second connection portions 8, 14 have been disclosed as T-shaped profiles. This is the most common cross section of a connection rail of an examination table. The skilled person would understand that the cross sections of the first and second connection portions 8, 14 may be adapted to other profiles of the connection rail with remained function and within the frames of the invention. As an alternative to the second connecting portion 14 being a protrusion 15, it would be obvious to the skilled person that it could be replaced by a groove and that any objects to be mounted thereto comprises a protrusion adapted to engage such groove Thus an object to be mounted in such groove could as such form a T-profile and hence mimic a connection rail of the examination table.

The base profile 7, the first connector 11 and the second connection 13 may all be provided as extruded profiles made by plastic or a light weight metal such as aluminum and be cut into lengths depending on a specific installation.

The shielding panels 10, 12 are made of a material that protects against radiation, such as a lead based material. Examples of lead based material are lead glass, lead acrylic, lead vinyl or lead rubber.

The first shielding panel 10 which is intended to extend from the examination table 1 towards the floor may be made of a flexible material or a combination of a rigid and flexible material. The second shielding panel 12 is preferably made of a rigid, self-supporting material. The material may be transparent, whereby the operator may stand behind the shield and look down in the radiant zone through the radiation-protective shielding.

To facilitate handling of the shielding panels 10, 12 both in terms of weight and size, each shielding panel preferably has a length that is smaller than the length of the examination table 1. It is preferred that two to four shielding panels 10, 12 are arranged side by side along the base profile 7.

The skilled person will understand that the cross sections of the base profile 7 and the first and second connectors 11, 13 may be changed with remained function and any such changes fall within the scope of the claimed invention.

Figure 5A:
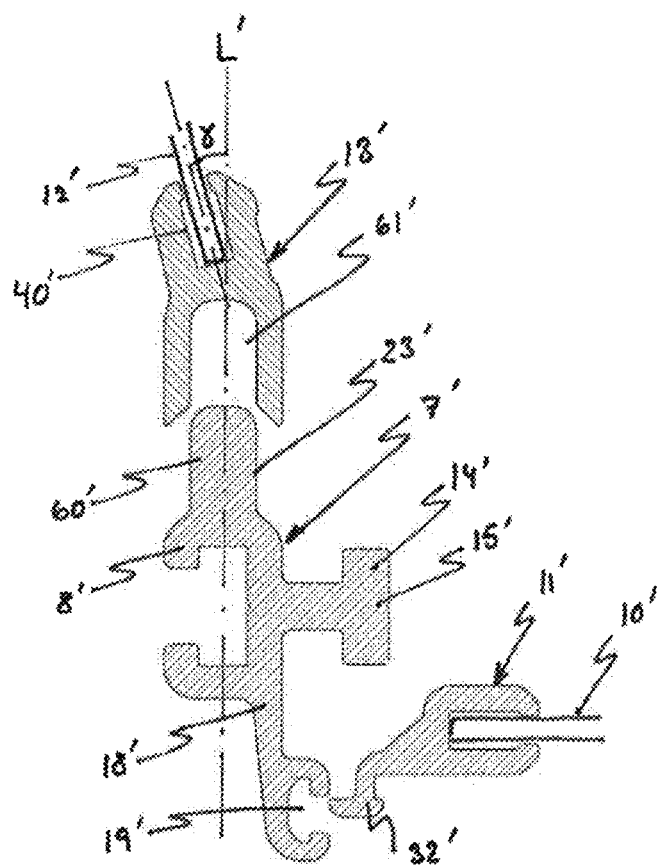
FIGS. 5A-5C discloses a second embodiment of the lower-body radiation protection system.
Figure 5B:
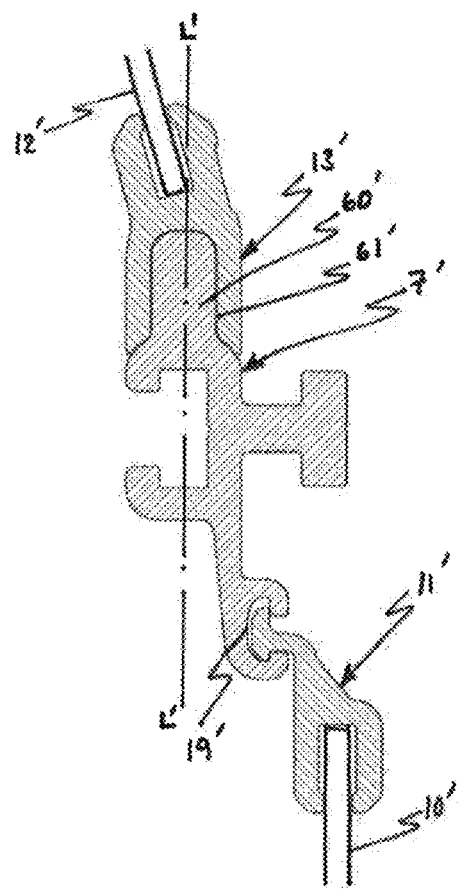
Figure 5C:
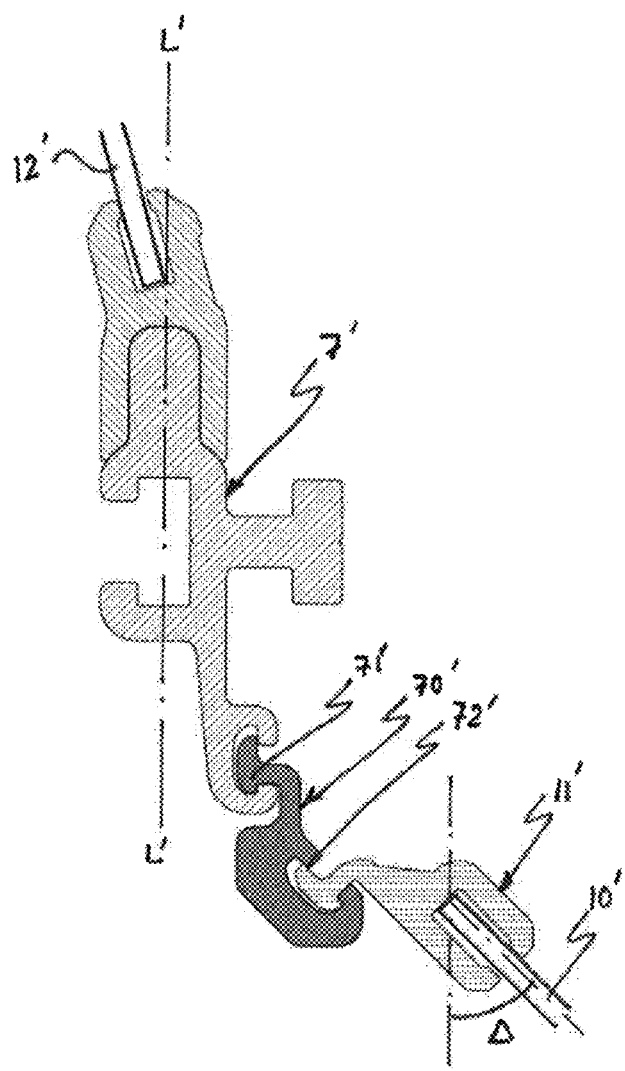

Now turning to FIGS. 5A-5C another embodiment of a lower-body radiation protection system is disclosed. FIG. 5A discloses the components before mounting and FIG. 5B discloses the components after mounting. Further, FIG. 5C discloses the use of an adaptor profile 70'.

The system comprises an elongated base profile 7', a first connector 11', a second connector 13' and the optional adaptor profile 70'. The first connector 11', the second connector 13' and the adaptor profile 70' are all formed as elongated profiles.

The elongated base profile 7' differs from the previously described base profile 7 in the design of the third connecting portion 18' and the fourth connecting portion 23'. The elongated base profile 7' comprises a first connecting portion 8' adapted to engage a connection rail 4 of an examination table 1. The elongated base profile 7' further comprises a second connecting portion 14' forming a protrusion 15'. The protrusion 15' can be replaced by a groove extending along the longitudinal extension of the elongated base profile 7'. The protrusion 15' is adapted to form a connection rail 4. In case of a groove, such groove is adapted to support a separate connection rail or a separate connector.

The fourth connecting portion 23' comprises a projection 60' having an extension coinciding with the center axis L' of the elongated base profile 7'. The projection 60' is configured to form a mount onto which the second connector 13' is to be mounted. The second connector 13' comprises a mating recess 61' having a cross section corresponding to the cross section of the projection 60'. Thus, the second connector 13' is adapted to be mounted to the fourth connecting portion 23' by a linear movement in parallel with the center axis L'.

The second connector 13' comprises a recess 40'. The recess 40' has an essentially rectangular cross section adapted to receive an edge of a second shielding panel 12'. The recess 40' may have, as seen in a cross section, a longitudinal extension forming an angle γ to the centre axis L' of the elongated base profile 7'. It is to be understood that the recess 40', with remained function may have an extension coinciding with the centre axis L'.

Now turning to the third connecting portion 18' of the elongated profile 7'. The third connecting portion 18' comprises a recess 19' allowing mounting of the first connector 11' supporting a first shielding panel 10'. The first connector 11' and the recess 19' have essentially the same design as that previously described and to avoid undue repetition, reference is made to the paragraphs above relating to FIGS. 1-4. When the first connector 11' is mounted to the recess 19', the first shielding panel 10' will be oriented in an essentially vertical position, see FIG. 5B.

Now turning to FIG. 5C. Should another angle be wanted to the first shielding panel 10', the adaptor profile 70' may be used. The adaptor profile 70' comprises a protrusion 71' having a design corresponding to the protrusion 32 of the first connector 11 previously described with reference to FIGS. 1-4. Also, the adaptor profile 70' comprises a recess 72' having a design corresponding to the recess 19B of the elongated profile 7 previously described with reference to FIGS. 1-4. Accordingly, instead of integrating the recess 19B in the elongated profile 7, the recess 72' is integrated in the adaptor profile 70'. Should the operator want to mount the first shielding panel 10' with an angle Δ to the centre axis L' of the elongated profile 7', the adaptor profile 70' is mounted directly to the elongated profile 7' and then the first connector 11' with the non-disclosed first shielding panel 10' is mounted to the adaptor profile 70'. When not in use, the adaptor profile 70' can be stowed away.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A lower-body radiation protection system, comprising:
    an elongated base profile including
        a first connecting portion including a first recess adapted to engage a connection rail of an examination table such that the elongated base profile is attached to the examination table via the first recess of the first connecting portion,
        a second connecting portion forming a protrusion or a groove extending along the longitudinal extension of the elongated base profile, wherein the protrusion is adapted to form a connection rail, and wherein the groove is adapted to support a separate connection rail or a separate connector, and
        a third connecting portion including a second recess;
    a first shielding panel configured to protect an operator from radiation; and
    a first connector supporting the first shielding panel, the first connector being adapted to be connected to the third connecting portion of the elongated base profile such that the first shielding panel is attached to the second recess of the third connecting portion of the elongated base profile via the first connector, wherein
    the first recess and the second recess are arranged on opposite sides of a longitudinal center axis L of the elongated base profile, such that the first recess is provided only on a first side of the longitudinal center axis L of the elongated base profile and the second recess is provided only on a second side of the longitudinal center axis L of the elongated base profile, the first side being a side closer to the examination table and the second side being a side further from the examination table when the elongated base profile is attached to the examination table.

2. The lower-body radiation protection system according to claim 1, wherein
    the first connecting portion and the second connecting portion are arranged on opposite sides of the longitudinal center axis L of the elongated base profile.

3. The lower-body radiation protection system according to claim 1, wherein
    the first connecting portion is formed by the first recess having a cross sectional shape complementary to the cross sectional shape of the connection rail of the examination table, and wherein the first recess is adapted to engage the connection rail of the examination table.

4. The lower-body radiation protection system according to claim 1, wherein
    the protrusion formed by the second connecting portion has a cross sectional profile corresponding to the cross sectional profile of the connection rail of the examination table.

5. The lower-body radiation protection system according to claim 1, wherein
    the first connector of the first shielding panel comprises a protrusion, whereby
    the first connector supporting the first shielding panel is arranged to engage the third connecting portion by the protrusion being inserted into the second recess by a linear movement and then pivoted inside the second recess into a locking position.

6. The lower-body radiation protection system according to claim 5, wherein
    the third connecting portion comprises at least two recesses, each recess allowing a major surface of the first shielding panel to extend in a preset angle Δ in view of a horizontal direction in a position when the first connector supporting the first shielding panel is set to a locking position.

7. The lower-body radiation protection system according to claim 1, wherein
    the elongated base profile further comprises a fourth connecting portion adapted to engage a second connector supporting a second shielding panel.

8. The lower-body radiation protection system according to claim 7, further comprising a second connector of the second shielding panel, the second connector being adapted to be connected to the fourth connecting portion of the elongated base profile.

9. The lower-body radiation protection system according to claim 1, wherein
the first connector is adapted to be connected to the third connecting portion of the elongated base profile via an adaptor profile.

10. The lower-body radiation protection system according to claim 1, further comprising the examination table.

11. The lower-body radiation protection system according to claim 7, further comprising the second shielding panel.

* * * * *